United States Patent [19]
Cazenave

[11] Patent Number: 5,879,320
[45] Date of Patent: Mar. 9, 1999

[54] IMPLANTABLE VASCULAR DEVICE

[76] Inventor: Craig Richard Cazenave, 2601 Ferol La., Lynn Haven, Fla. 32444

[21] Appl. No.: 771,894
[22] Filed: Dec. 23, 1996
[51] Int. Cl.⁶ .................................................. A61M 5/00
[52] U.S. Cl. ...................................................... 604/8; 623/1
[58] Field of Search ................................... 604/4–6, 8–9, 604/10, 98, 96, 101, 102, 264, 280, 191, 192, 194; 623/1

[56] References Cited

U.S. PATENT DOCUMENTS

| 3,626,938 | 12/1971 | Versaci | 128/214 |
| 4,447,237 | 5/1984 | Frisch et al. | 604/175 |
| 5,411,479 | 5/1995 | Bodden | 604/98 |
| 5,562,617 | 10/1996 | Finch, Jr. et al. | 604/93 |

Primary Examiner—John G. Weiss
Assistant Examiner—Ki Yong O
Attorney, Agent, or Firm—Carnes Cona & Dixon

[57] ABSTRACT

The present invention is an implantable vascular device which has the ability to open and close without the formation of thrombi. The device comprises at least one shunt which maintains a valve system. This shunt is surgically grafted to a blood line for enabling fluid flow through the shunt when the valve system is in an opened state. This will provide a device which is well suited for use in hemodialysis because the shunt can be opened for hemodialysis and closed when not in use. The destructive problems associated with the high flow states is limited only to the short time interval of the hemodialysis.

19 Claims, 3 Drawing Sheets

IMPLANTABLE VASCULAR DEVICE

BACKGROUND OF THE INVENTION

1. Field of the Invention

The present invention relates generally to an implantable vascular device and more particularly to an implantable vascular shunt device which would increase the life of a hemodialysis graft and will eliminate problems typical of conventional implantable vascular devices, such as venous thrombosis, high output failure and limb morbidity.

2. Description of the Prior Art

Patients suffering from rental failure are treated by hemodialysis. Hemodialysis is a process wherein a machine is utilize for removal of life-threatening chemicals from the blood stream, since the patient's kidneys cannot successfully remove these chemicals. In order to allow these machines to work, an access to the patients blood flow is required.

Accordingly, a multiplicity of vascular access devices have been designed and implemented which create an artificial fistula between an artery and vein. Typically, these conventional devices are comprised of an graft material that bridges between an artery and vein creating a communication or fistula. One end of the graft is secured to a vessel, such as the device disclosed in U.S. Pat. No. 3,713,441, issued to Thomas. Unfortunately, due to the design and configuration of these devices, such as the one disclosed in Thomas, they are cause prolonged high flow states that can result in damage to the venous wall which leads to occlusion of the vein and thrombosis of the fistula. Due to the high flow state within the veins, these devices can cause several problems other than venous occlusion, such as arterial stenosis, limb swelling and heart failure. When shunt occlusion or thrombosis occurs, another vein segment must be found surgically and a shunt revision performed. The process is repeated at each occurrence of shunt occlusion or thrombosis. Repeated failures will result in complete replacement of the fistula puncturing of the shunt will result failure of the graft material. This process can be extremely costly to the patient and society.

Unfortunately, graft failure is inevitable due to shear forces from high velocity turbulence of blood flow on the venous walls which causes endothelial damage in the form of endothelial hypertrophy (venous wall scaring). Problems that arise from the fistula can limit or hinder the process of hemodialysis, thereby causing severe or fatal consequences to the individual suffering from renal disease.

Accordingly, research has shown that none of these previous efforts provide the benefits intended with the present invention, such as providing a dialysis graft that provides flow rates necessary for dialysis and yet limit the trauma endured by venous walls. Additionally, prior techniques do not suggest the present inventive combination of component elements as disclosed and claimed herein. The present invention achieves its intended purposes, objectives and advantages over the prior art device through a new, useful and unobvious combination of component elements, which is simple to use, with the utilization of a minimum number of functioning parts, at a reasonable cost to manufacture, assemble, and test.

SUMMARY OF THE INVENTION

The present invention provides an implantable vascular device having the unique ability to open and close the graft without the formation of thrombi (clots) which can lead to complications such as limb loss. Because the device can be opened for hemodialysis and closed when not in use, the destructive problems associated with the high flow states is limited only to the short time interval of the hemodialysis.

The present invention is an artery to vein shunt which is well suited for use in hemodialysis. As such, two embodiments for the device is disclosed. The first embodiment includes devices or housings which are grafted between an artery and a vein with the more traditional tube graft. In the second embodiment, a single device or housing is grafted between a vein without an intervening tube graft.

The first embodiment of the present invention includes a "tube" type shunt having two valves assemblies or two housing having a valve located therein are provided with an intervening GORTEX™ "tube" graft. The first housing is a venous valve for coupling to a vein via a graft or cuff, such as DACRON™ or GORTEX™ (also known as terylene or e-PTFE), and the second housing is an arterial valve coupled to an artery via a graft or cuff, such as DACRON™ or GORTEX™. This will provide for the venous valve to be placed at some distance from the arterial valve, thus allowing the surgeon to "find" a suitable vein for the venous return if one is not available adjacent to the artery. The intervening GORTEX™ "tube" graft couples the venous valve to the arterial valve.

Each housing or valve assembly further includes a first opening on one side wall and a second opening located on the opposite wall of the housing. This second opening is aligned with the first opening. Secured to the encompassing area of the openings is the cuff or graft which is fabricated from a durable material, such as DACRON™ or GORTEX™.

A slide bolt extends horizontally through the housing and acts as a valve for opening and closing the passage between the two openings in the housing's face or side walls. The bolt includes a handle which extends upwardly from a channel in the top wall of the housing. This handle can slide freely within the channel. The slide bolt is provided with an aperture which extends horizontally therethrough. When the bolt is in the open position, this aperture is in alignment with the openings on either side of the housing, thus creating a channel between the artery and vein.

Covering and protecting the handle is a lid. This lid will prevent fibrous in-growth which could clog the handle to render the bolt inoperative. The lid is fabricated from a pliable material to enable a technician or the like to feel the handle. Once the handle is felt, the technician can press on the handle and slide it accordingly, into the open or closed position.

The tube is secured to the second hole of the first housing (arterial valve) and the second hole of the second housing (the venous valve). In this way, a first shunt device would be more applicable for the groin and the second shunt device for the forearm. The dialysis for the first device would be via a venous patch graft, secured to the upper surface of the common femoral vein. During hemodialysis it is advantageous to direct fluid flow upwards onto the patch graft surface further reducing the damage to veins.

The second embodiment of the present invention or the fistula device, is basically a single housing or valve. In this embodiment, the device is simplified by the removal of one valve assembly and the GORTEX™ tube. The housing is surgically grafted to the exterior of an artery wall via a graft or cuff, such as DACRON™ or GORTEX™, which is cemented to the housing.

This graft material is surgically sewn to the artery on one side of the housing and to the vein on the other side of the housing, thus creating the fistula with an intervening valve assembly (the housing and slide bolt. Thereby eliminating the need of the GORTEX™ tube and second housing.

The housing(s) used in the first and second embodiments is/are preferably constructed from a durable, non-corrosive and non-thrombogenic material, such as stainless steel. The bolt, like the housing and seal, is fabricated from or coated with a non-thrombogenic material which are commonly employed in surgical procedures.

The housing(s) is/are preferably constructed from a durable, non-corrosive and non-irritating materials, such as surgical stainless steel. The bolt should be fabricated from or coated with a non-thrombogenic material such as TEFLON (polytetraflouroethlyene-PTFE). Since the housing, bolt and seal are minimal in size and dimension there should be no physical discomfort.

Thrombosis within the arterial system is limited by maintaining laminar flow. This is accomplished by reducing the turbulence caused by standard grafting techniques. The anatamosis of the artery to the housing is done by a very small cuff of graft material sewn end to end unique a technique of outside to inside to outside stitching. This is performed by making a parallel incision to the long axis of the artery on the opposite side from the anastamosis. This allows the surgeon to see the "inside" of the artery and to closely apply the wall of the artery to the valve housing. The parallel incision is then closed using standard vascular techniques.

Additionally, a small amount of clot will be formed within the channel of the bolt but due to the small dimensions of the device, the amount of thrombi presented to the lungs when the shunt is opened will be small.

For utilizing the apparatus of the present invention, the first device, and if needed, the second device are surgically grafted onto the artery and vein, respectively, via an attaching means. After the patient has healed, the individual is ready for dialysis. The dialysis technician would open the valve via the handle, which is palpable under the skin. Thereby, providing for fluid communication to exist between the artery and the vein via the first and second opening within the valve housing. The tubing from the dialysis machine can be coupled to the fistula via normal means. When the fistula is not in use, the shunt is closed and the dialysis machinery uncoupled in the usual fashion.

Accordingly, it is the object of the present invention to provide for an implantable vascular device which will overcome the deficiencies, shortcomings, and drawbacks of prior implantable vascular device and methods thereof.

It is yet another object of the present invention to provide for an implantable vascular device which is well suited for use in hemodialysis and which will provide a shunt that is durable and increased the life expediency of the fistula over prior devices.

Still a further object of the present invention is to provide an implantable vascular device for hemodialysis which substantially decreases or eliminates common problem typical of prior devices, such as arterial emboli, pulmonary emboli and arterial and venous thrombosis.

It is still another object of the present invention, to be specifically enumerated herein, to provide an implantable vascular device in accordance with the preceding objects and which will conform to conventional forms of manufacture, be of simple construction and easy to use so as to provide a device that would be economically feasible, long lasting and relatively trouble free in operation.

Although there have been many inventions related to implantable vascular devices, none of the inventions have become sufficiently compact, low cost, and reliable enough to become commonly used. The present invention meets the requirements of the simplified design, compact size, low initial cost, low operating cost, ease of installation and maintainability, and minimal amount of training to successfully employ the invention.

The foregoing has outlined some of the more pertinent objects of the invention. These objects should be construed to be merely illustrative of some of the more prominent features and application of the intended invention. Many other beneficial results can be obtained by applying the disclosed invention in a different manner or modifying the invention within the scope of the disclosure. Accordingly, a fuller understanding of the invention may be had by referring to the detailed description of the preferred embodiments in addition to the scope of the invention defined by the claims taken in conjunction with the accompanying drawings.

BRIEF DESCRIPTION OF THE DRAWINGS

Similar reference numerals refer to similar parts throughout the several views of the drawings.

DESCRIPTION OF THE PREFERRED EMBODIMENTS

Figure 1:
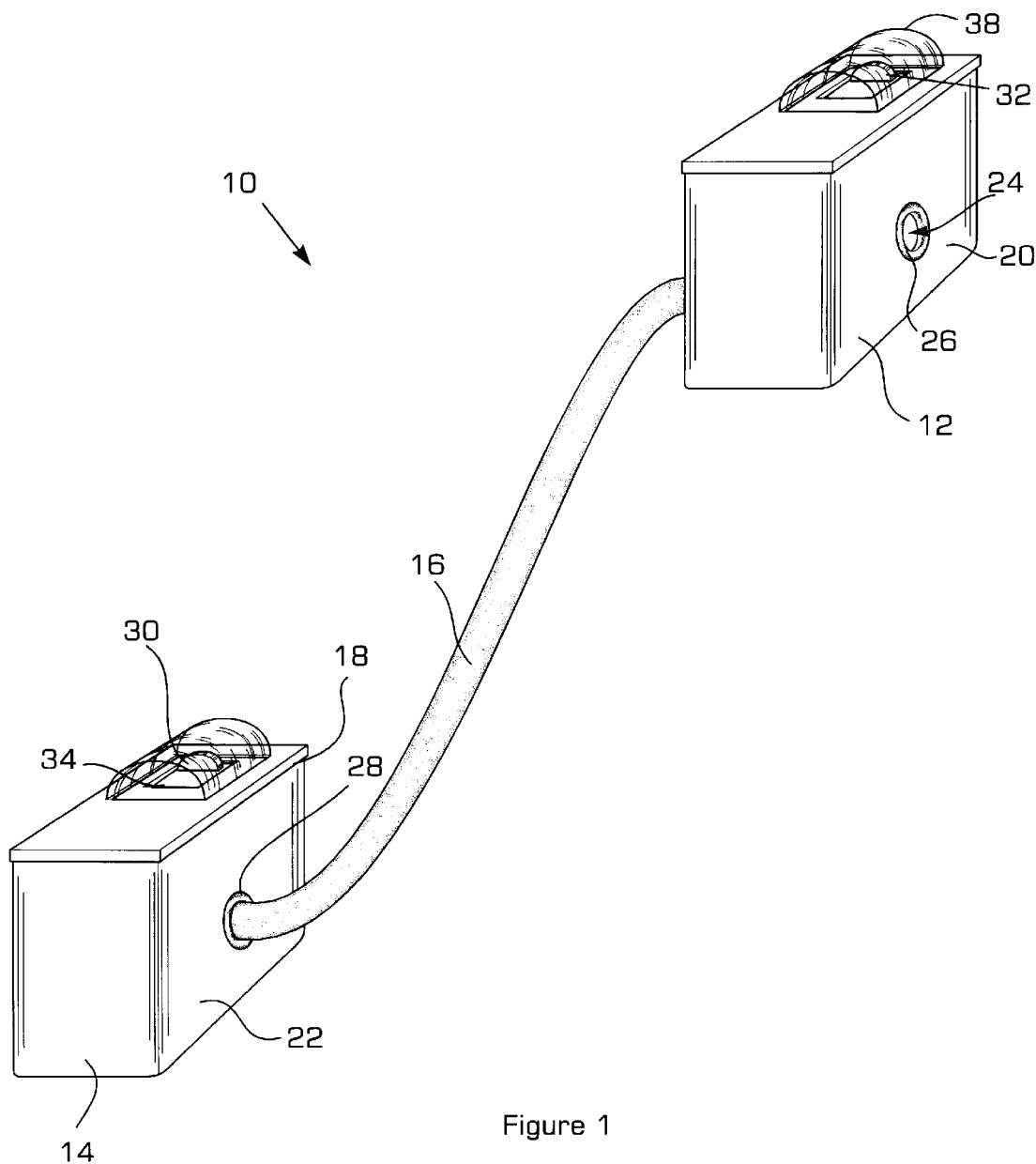
FIG. 1 is a perspective view of the implantable vascular device of the present invention.
Figure 2:
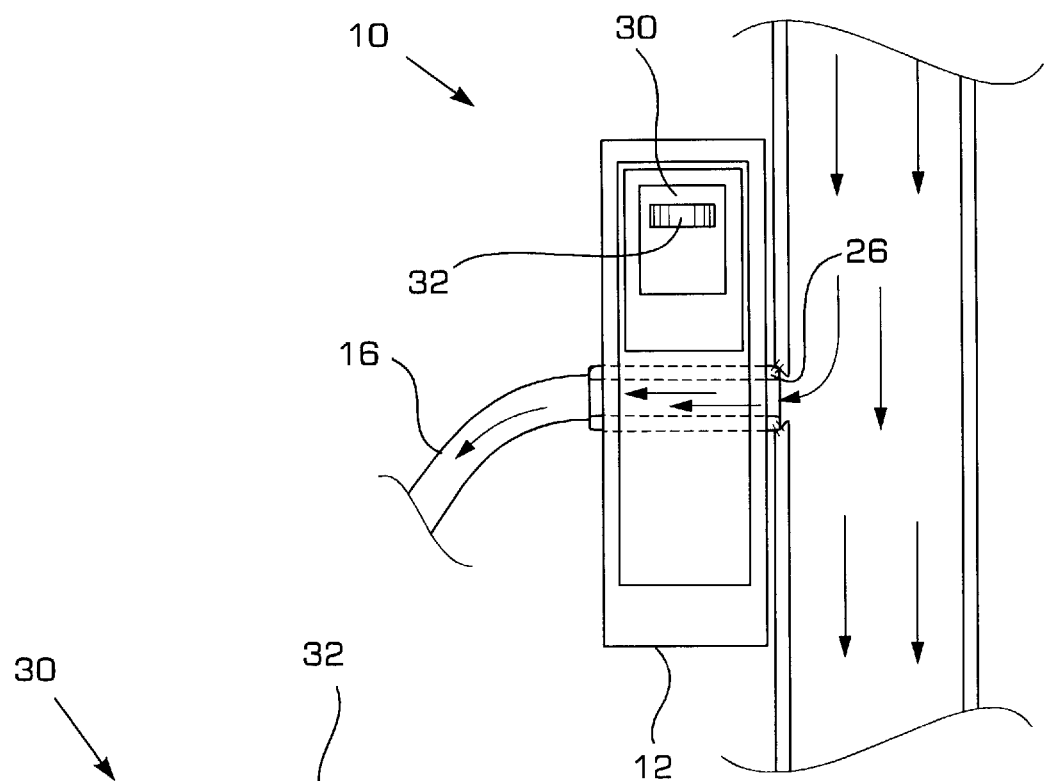
FIG. 2 is a cross sectional view the first device of the implantable vascular device secured to an artery.
Figure 3:
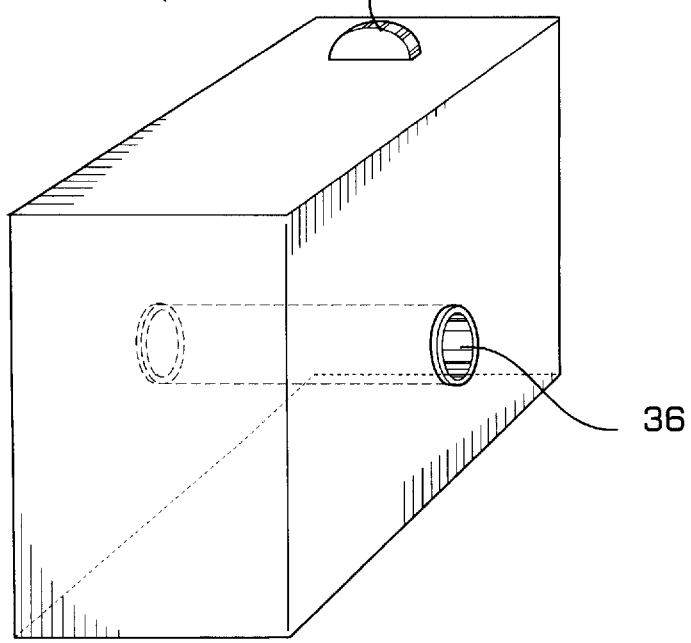
FIG. 3 is a detail view of the valve used in the first and/or second device of the implantable vascular device of the present invention.

With reference to drawings, and in particular to FIGS. 1–3 thereof, the present invention will be described. As seen, the first embodiment of the implantable vascular device 10 of the present invention provides for an apparatus which includes a valve mechanism for manually opening and closing the device when desirable. In the open state the device is ready for hemodialysis while in the closed state fluid communication is prohibited in the graft tube 16. As seen in FIGS. 1–3, the implantable vascular device 10 of the present invention comprises a first device 12 coupled to a second device 14 via an graft tube 16.

The first device 12 is designed to be affixed adjacent to an artery to provide for the first device to connect arterial side of the shunt. The second device 14 is designed to be affixed adjacent to a vein to provide for the second device for the second connection to the venous side of the shunt.

For the purpose of illustration, the first and second devices are shown to be rectangular. However, the devices can take any shape or configuration so as to provide for a device which can be manufactured easily and economically, as well as provide a device which can be maintained comfortably under the skin.

Each device or shunt 12 and 14, respectively, is basically a housing having an upper portion 18, a first side 20 and a second side 22. Extending through the first side 20 of each shunt 12, 14 is a first opening 24. Secured to the outer area of the first opening 24 is a seal or graft 26. This seal or graft 26 is adapted to be surgically secured to the blood line. As such the graft 26 of the first device 12 is surgically secured to the artery to provide for arterial anastamosis while the graft 26 of the second device 14 is surgically secured to the vein to provide for venous anastamosis. The graft 26 is configured to be long-lasting and to properly seal the devices to the blood line for preventing fluid leakage. As such, the graft 26 must be fabricated from a durable and non-thrombogenic material, such as DACRON™ or GORTEX™ (also known as terylene or e-PTFE membrane). Hence, it is seen that an aperture is formed in the vein and artery. The first opening is adapted to align with the vein or artery for providing a fluid communication means between the shunts and blood lines when the valve assemblies or housings are in an opened position.

A second opening 28 is located on the second side 22 of each device 12 and 14, respectively. This second opening 28 is adapted to be in fluid communication with the first opening 24 when the device is in an opened state. As seen in the figures, the graft tube 16 is secured to second opening 28 for providing for the second side 22 of the arterial shunt 12 to face the second side 22 of the venous shunt 14.

A slide bolt 30 is housed and maintained within each shunt 12 and 14. The bolt 30 includes a handle 32 which extends upwardly through a slide window 34 located on the upper portion 18 of each device 12 and 14. This slide window 34 enables the handle to linearly move or slide freely. Extending horizontally through the slide plate is a channel 36 which is adapted to align with the first opening 24 and second opening 28 when the device is in an opened state. Accordingly, moving the handle in a first direction, such as upwardly, will provide for the channel 36 to align with the first and second openings for rendering proper fluid communication between the arterial shunt and the venous shunt. Moving the handle in a second and opposite direction, such as downwardly, will provide for the channel 36 to relocated and cause a solid portion of the bolt to be between the first and second openings of the first and second device. Thereby, prohibiting fluid flow. As seen, this slide bolt 30 acts as a valve mechanism.

For preventing blockage or clogs within the slide window 34 and handle 32, a lid 38 can be provided. The lid should be made from a flexible and pliable material so as to provide for the handle to be palpable under the skin. This will allow a technician, or the like, to manually open or close the device. The lid can extend across the entire upper portion 18 of the shunts or can partially extend across the upper portion 18 of the device for minimally covering the window 34.

Prior to utilizing the device of the present invention, the artery and vein are opened via conventional methods for providing an orifice to exist in the artery and vein, respectively. The graft 26 of the arterial shunt 12 of the implantable vascular device 10 is secured to the orifice of the artery using a novel attaching process.

The process is performed by making a parallel incision to the long axis of the artery on the opposite side from the anastamosis. This allows the surgeon to see the "inside" of the artery and to closely apply the wall of the artery to the valve housing. The parallel incision is then closed using standard vascular techniques.

The next step is to surgically attach the graft 26 of the venous shunt to the orifice of the vein via the attaching process of standard venoplasty. After the patient has healed from surgery, hemodialysis can be performed. The technician secures the appropriate tubing from the dialysis machinery to the graft tube 16. The valve mechanism of the first and second devices are then switched to the opened position manually. In order to do so, the handles 32 of the arterial shunt and venous shunt are pulled to the opened position to enable proper fluid flow.

Alternatively, for areas where the artery and vein are situated side-by-side, such as the groin area, the graft tube is eliminated to provide for a second embodiment of the present invention. This second embodiment is illustrated in further detail in FIG. 4 and as seen the implantable vascular device 10 of the present invention comprises a first device 12 which is similar is structure as the device 12 illustrated and discussed in FIGS. 1–3. As such, this device 12 includes a first opening 24 extending through a first side of the device or housing 12. A valve is maintained within the housing. Located on the opposite side of the first opening is a second opening 28 which is situated on the second side 22 of the device 12.

Secured to the outer area of the first opening and second opening is a graft or cuff 26. The graft or cuff that is secured to the first opening is adapted to be secured to the artery while the graft or cuff which is secured to the second opening is adapted to be secured to a vein. Thereby, a fluid communication means is established between the artery and vein when the valve is in an opened position. Hence, the valve provides creates the fistula between the artery and vein.

Optionally, for aiding in the placement and securment of the venous shunt to the artery, a securing means extends outwardly from the second side 22 of the housing. This securing means comprises an extension 40 which is secured to the upper portion 18 of the device. The extension is adapted to be secured to the upper surface of the vein and as such, the extension 40 can be curved for easily encompassing the vein. This extension is sutured onto the vein by way of conventional surgical techniques of venoplasty.

A slide bolt 30 having a handle 32 is housed and maintained within the device 12. The handle extends upwardly from the housing 12 via a window 36. A lid 38 protects and covers the handle and lid and may optionally cover the entire upper surface of the device 12.

Extending through the bolt 30 is a channel. When the bolt is in an opened position, the channel is aligned with the first opening and second opening for enabling fluid flow. When the bolt is in a closed position, a blockage exists between the first opening 24 and second opening 28. Thereby, the slide bolt having a channel therethrough provides for a valve.

Figure 4:
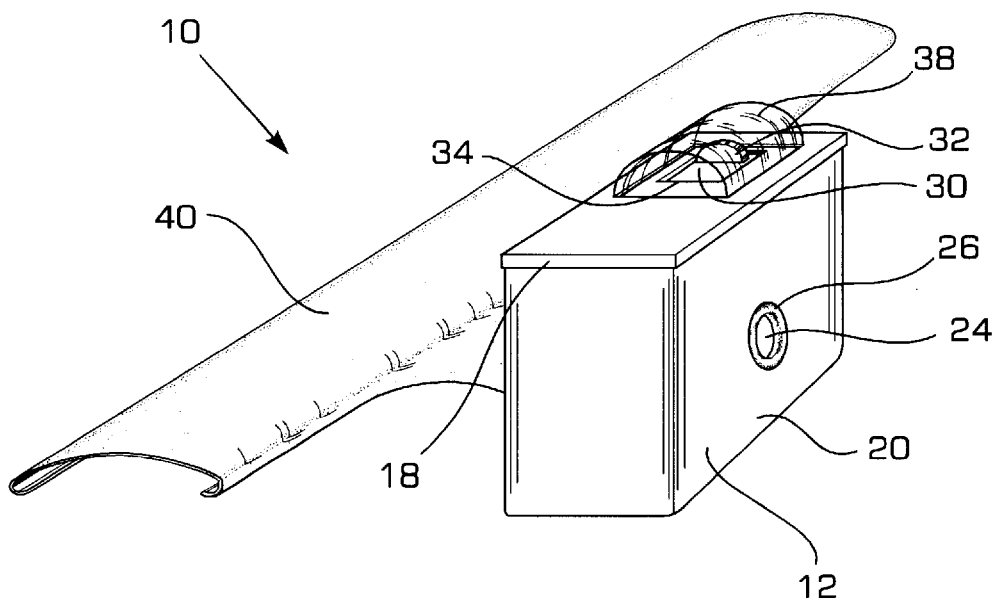
FIG. 4 is a detailed view of the second embodiment of the implantable vascular device of the present invention. This figure also illustrates a second embodiment for the venous shunt used in the implantable vascular device of the first embodiment.

It is noted that the second device or venous shunt 14 in the first embodiment, illustrated in FIGS. 1–3, can be altered to include the extension 40 as discussed in FIG. 4. This will offer more security of the device 14 to the vein.

The materials utilized for the housings of the first and second embodiments must be non-corrosive and non-irritating, such as surgical stainless steel. The bolt should be fabricated from or coated with a non-thrombogenic material such as Teflon.

Additionally, these embodiments illustrated in FIGS. 1–4 disclosed shunts which must be minimal in size. Typically, to reduce the amount of thrombi sent to the lungs each time the graft is opened, the shunts, including the bolt, would be less than one centimeter in length and width. This would provide for a total thrombotic load to be less than 0.5 cubic centimeter.

Since this device of the present invention addresses the graphs and applies a valve system to the graft, it can be understood that these device can be utilized with conventional vascular access fistula devices. Thereby, providing a graph system which can easily be retrofitted into existing fistula devices and methods thereof.

Optionally, this housing as disclosed can also be attached to the fistula to provide for the fistula, like the artery and vein, to have a valve system attached thereto.

The product of the present invention will sufficiently prolong the life of dialysis graft which will inherently prolong the life of the vascular access devices.

While the invention has been particularly shown and described with reference to an embodiment thereof, it will be understood by those skilled in the art that various changes in form and detail may be made without departing from the spirit and scope of the invention.

I claim:

1. An implantable vascular device to be implanted in a living body to facilitate access to a fluid path with the living body, said implantable vascular device comprising:

an arterial shunt having a first valve, being slidable for surgically coupling exteriorly to at least one blood line and including a fluid communication means for enabling fluid flow from said at least one blood line and through said arterial shunt when said valve being slid in an opened position, providing a fistula with said valve;

said valve being slidable linearly;

said valve including an activating means for opening and closing said valve;

a first pliable and flexible lid being provided on said arterial shunt for protecting and covering said activating means of said first valve and said first pliable lid provides a smooth outer surface for preventing protrusion of said activating means of said slidable valve and for preventing fibrous in-growth in and around said activating means and said arterial shunt; and said pliable and flexible lid enabling said activating means to be palpable under skin so as to manually open or close said slidable valve.

2. An implantable vascular device as in claim 1 further comprising a securing means located on said arterial shunt, said securing means having an extension which extends outwardly from a side of said arterial shunt, and said extension for surgically securing to a top surface of a fluid line.

3. An implantable vascular device as in claim 1 further comprising a venous shunt having a second valve for surgically coupling to a vein and said second valve having a second fluid communication means for enabling fluid flow from said vein into said venous shunt when said second valve is in an opened position, said arterial shunt for surgically coupling to an artery, and a flexible tube coupling said arterial shunt to said venous shunt for providing fluid communication between said arterial shunt and said venous shunt when said first valve and said second valve are in an opened position.

4. An implantable vascular device as in claim 3 wherein said venous shunt further includes a second pliable lid, said second pliable lid being located on said venous shunt for protecting and covering said second valve and said second pliable lid providing a smooth outer surface for preventing protrusion of said second valve and for preventing fibrous in-growth.

5. An implantable vascular device as in claim 1 wherein said arterial shunt includes a first opening and a second opening, a first graft surrounds said first opening, a second graft surrounds said second opening, said first graft capable of surgically coupling to a first blood line having an aperture therethrough for providing said aperture to be aligned with said first opening, said second opening capable of surgically coupling to a second blood line having an aperture therethrough for aligning said aperture to said second opening, and a slide bolt having a channel therethrough being maintained within said arterial shunt, said channel being aligned with said first opening and said second opening when said slide bolt is in an opened position for providing said fluid communication means, and said channel being dis-aligned with said first opening and said second opening when said slide bolt is in a closed position.

6. An implantable vascular device to be implanted in a living body to facilitate access to a fluid path with the living body, said implantable vascular device comprising:

an arterial shunt having a first valve for surgically coupling to an exterior of an artery and includes a fluid communication means for enabling fluid flow from the artery and through said arterial shunt when said valve is in an opened position and providing a fistula with said valve;

a venous shunt having a second valve for surgically coupling to a vein and includes a second fluid communication means for enabling fluid flow from said vein into said venous shunt when said second valve is in an opened position;

a tube having a coupling between said arterial shunt to said venous shunt to provide for fluid communication between said arterial shunt and said venous shunt when said first valve and said second valve are in an opened position; and a first pliable lid being provided on said arterial shunt for protecting and covering said first valve and said first pliable lid providing a smooth outer surface for preventing protrusion of said first valve and for preventing fibrous in-growth, and a second pliable lid being provided on said venous shunt for protecting and covering said second valve and for preventing fibrous in-growth.

7. An implantable vascular device as in claim 6 wherein a first aperture is capable of being located in the artery and a second aperture is capable of being located in the vein, said arterial shunt and said venous shunt each include a first side having a first opening and a second side including a second opening, said first opening of said arterial shunt capable of aligning with said first aperture, said first opening of said venous shunt capable of aligning with the second aperture, said second opening of said arterial shunt being coupled to a first end of said tube, said second opening of said venous shunt being coupled to a second end of said tube, said first orifice and said first opening of said arterial shunt providing for said fluid communication means and said second orifice and first opening of said venous shunt providing for said second fluid communication means.

8. An implantable vascular device as in claim 7 where a graft being secured to said first opening of said arterial shunt and to said second opening of said venous shunt for providing a first graft being located between and attached to said first opening of said arterial shunt and the first aperture, and a second graft being located between and attached to said first opening of said venous shunt and the second aperture.

9. An implantable vascular device 8 wherein a third graft being secured to said second opening of said arterial shunt and a fourth graft being secured to said second opening of said venous shunt for providing said third graft being located between and attached to said second opening of said arterial shunt and said first end of said tube, and said fourth graft being located between and capable of being attached to said second opening of said venous shunt and said second end of said tube.

10. An implantable vascular device as in claim 9 wherein said first graft, said second graft, said third graft, and said fourth graft are fabricated from e-polytetraflouroethylene or terylene.

11. An implantable vascular device as in claim 7 wherein said first valve comprises a first slide bolt being housed and maintained within said arterial shunt, said second valve comprises a second slide bolt being housed and maintained within said venous shunt, said first bolt having a first channel extending therethrough, said second bolt having a second channel extending therethrough, said first channel being aligned with said first opening and said second opening of said arterial shunt to provide for said first valve to be in an opened position, and said second channel is aligned with said first opening and said second opening of said venous shunt to provide for said second valve to be in an opened position.

12. An implantable vascular device as in claim 1 wherein said valve being fabricated from a non-thrombogenic material.

13. An implantable vascular device as in claim 1 wherein said arterial shunt being fabricated from a non-corrosive and non-irritating material.

14. An implantable vascular device as in claim 1 wherein a handle extending upwardly from a window of said arterial shunt, said handle providing for said valve to be in an opened or closed position, and said first pliable lid covers and protects said handle, said handle being said activating means.

15. An implantable vascular device as in claim 6 wherein a securing means being located on said arterial shunt and said venous shunt, said securing means having an extension extending outwardly from a side of said arterial shunt, and said extension being capable of surgically securing to a top surface of the blood line.

16. An implantable vascular device as in claim 6 wherein a securing means extending outwardly from and being secured to said arterial shunt or said venous shunt and said securing means including an extension, and said extension is capable of being surgically secured to a top surface of the blood line.

17. An implantable vascular device as in claim 6 wherein said arterial shunt and said venous shunt each include a window, a handle extends upwardly from said window to provide for an opening and closing means for said arterial shunt and said venous shunt, and said first pliable lid covers and protects said handle of said arterial shunt and said second pliable lid covers and protects said handle of said venous shunt.

18. An implantable vascular device as in claim 6 wherein said first valve and said second valve being fabricated from a non-thrombogenic material.

19. An implantable vascular device as in claim 6 wherein said arterial shunt and said venous shunt are fabricated from a non-corrosive and non-irritating material.

* * * * *